United States Patent [19]
Kadota et al.

[11] Patent Number: 5,858,695
[45] Date of Patent: Jan. 12, 1999

[54] METHOD OF QUANTITATIVE DETERMINATION OF BILIRUBIN AND A REAGENT THEREFOR

[75] Inventors: Akira Kadota, Sunto-gun; Kayoko Shigenobu, Mishima; Akira Miike, Sunto-gun; Kazuhito Miyauchi, Tagata-gun, all of Japan

[73] Assignee: Kyowa Medex Co., LTD., Tokyo, Japan

[21] Appl. No.: 736,058

[22] Filed: Oct. 22, 1996

[30] Foreign Application Priority Data

Oct. 27, 1995 [JP] Japan .................................. 5-280014

[51] Int. Cl.$^6$ ...................................................... C12Q 1/26
[52] U.S. Cl. ................ 435/25; 536/1.11; 435/4
[58] Field of Search ................ 435/25, 12, 39, 435/4; 536/1.11; 530/300

[56] References Cited

U.S. PATENT DOCUMENTS

| | | | |
|---|---|---|---|
| 4,311,665 | 1/1982 | Wu | 422/56 |
| 4,554,249 | 11/1985 | Kosaka et al. | 435/10 |
| 4,600,689 | 7/1986 | Matsui et al. | 435/25 |
| 4,638,208 | 1/1987 | Aoyama et al. | 436/12 |
| 4,681,841 | 7/1987 | Matsumoto | 435/18 |
| 4,839,279 | 6/1989 | Kosaka et al. | 435/25 |
| 5,104,794 | 4/1992 | Kondo et al. | 435/25 |
| 5,401,639 | 3/1995 | Saldivar, Jr. et al. | 435/14 |
| 5,563,072 | 10/1996 | Tokuda et al. | 936/97 |

FOREIGN PATENT DOCUMENTS

| | | |
|---|---|---|
| 0317243 | 5/1989 | European Pat. Off. . |
| 027656 | 3/1981 | Japan . |
| 159487 | 10/1982 | Japan . |
| 017999 | 1/1984 | Japan . |
| 63-052060 | 3/1988 | Japan . |
| 4267893 | 9/1992 | Japan . |

OTHER PUBLICATIONS

Clinical Chemistry, vol. 38, No. 2 (Feb. 1992) pp. 298–302.
Clinical Chemistry, vol. 34, No. 12, (Dec. 1988) p. 2581.

*Primary Examiner*—Gary E. Hollinden
*Assistant Examiner*—Dameron Jones
*Attorney, Agent, or Firm*—Fitzpatrick, Cella, Harper & Scinto

[57] ABSTRACT

Disclosed are a method for quantitative determination of bilirubin and a reagent for the method, which are useful in clinical examinations. The method comprises subjecting the bilirubin in a sample to coexist with ascorbate oxidase and a reaction promoter in aqueous medium to thereby oxidize the bilirubin, measuring the change in absorbance of the aqueous medium and comparing the change in absorbance with a calibration curve. The reagent comprises ascorbate oxidase and a reaction promoter.

26 Claims, 2 Drawing Sheets

METHOD OF QUANTITATIVE DETERMINATION OF BILIRUBIN AND A REAGENT THEREFOR

BACKGROUND OF THE INVENTION

The present invention relates to a method for quantitative determination of bilirubin and a reagent composition for quantitative determination of bilirubin, which are useful in clinical examinations.

Bilirubin is a physiological metabolite of heme and is a dye which is present most largely in bile. In serum, it exists in the direct form and in the indirect form, and it is extremely important to differentially determine the amount of direct bilirubin and indirect bilirubin in clinical examinations. The conventional method for differential determination of direct bilirubin and indirect bilirubin which has been carried out for a long time in clinical examinations, involves determination of total bilirubin and determination of direct bilirubin, and the indirect bilirubin is obtained by subtracting the direct bilirubin from the total bilirubin.

In quantitative determination of bilirubin by a chemical means, known is a method of colorimetrically measuring the amount of azobilirubin to be formed through the reaction of bilirubin with a diazo reagent. However, the method is problematic in that the operation is complicated and in that accurate data have not been obtained since the diazo reagent used reacts with some organic compounds other than bilirubin in sample.

On the other hand, in quantitative determination of bilirubin by an enzymatic means, known are methods using bilirubin oxidase derived from fungi belonging to the genus of Basidiomyctes (Japanese Published Unexamined Patent Application No. 27656/81) and microorganisms belonging to the genus of Myrothecium (Japanese Published Unexamined Patent Application No. 159487/82) which catalyze the oxidation of bilirubin. In the methods, standard solutions having varying concentrations of bilirubin to be reacted with the bilirubin oxidase give a calibration curve showing the relationship between the bilirubin concentration and the change in absorbance of the reaction mixture, and a sample having an unknown bilirubin concentration is reacted with the oxidase to give the concentration calculated by comparison of the measured change in absorbance with the calibration curve.

There has also been reported a method of quantitative determination of total bilirubin and direct bilirubin that uses an enzyme selected from the group consisting of bilirubin oxidase, ascorbate oxidase, laccase and tyrosinase, in the presence of a reaction promoter selected from the group consisting of surfactants, aromatic carboxylates, sulfa drugs and proteases (Japanese Published Unexamined Patent Application No. 17999/84).

The quantitative determination of bilirubin using enzyme is defective in the following points. Since bilirubin oxidase is unstable in an aqueous medium, a reagent containing bilirubin oxidase is often prepared in the form of a freeze-dried powder. The reagent must be dissolved in an aqueous medium just before use and the life of the prepared reagent is short. The other oxidases except bilirubin oxidase, such as ascorbate oxidase, etc., do not effectively oxidize bilirubin. Even if some known reaction promoters are added to these reagents, the oxidation of bilirubin is not promoted very much.

SUMMARY OF THE INVENTION

The present invention provides a method for quantitative determination of bilirubin in a sample, comprising the steps of (A), (B), (C) and (D):

(A) selecting a reaction promoter selected from the group consisting of a), b) and c):
  a) substituted aromatic hydrocarbon with at least two substituents which are independently selected from substituted amino, unsubstituted amino and hydroxyl,
  b) substituted aromatic heterocyclic compound with at least two substituents which are independently selected from substituted amino, unsubstituted amino and hydroxyl, and
  c) organic iron compound, (B) subjecting the bilirubin in the sample to coexist with ascorbate oxidase and the reaction promoter in an aqueous medium to thereby oxidize the bilirubin, (C) measuring a change in absorbance of the aqueous medium, and (D) comparing the change in absorbance with a calibration curve.

The present invention also provides a method for quantitative determination of bilirubin in a sample, comprising the steps of (A),(B),(C) and (D):

(A) selecting a precursor of reaction promoter selected from the group consisting of a) and b):
  a) substituted aromatic hydrocarbon with at least two substituents which are independently selected from substituted amino, unsubstituted amino and hydroxyl, and at least one of which substituents is protected with an enzymatically-removable protective group, and
  b) substituted aromatic heterocyclic compound with at least two substituents which are independently selected from substituted amino, unsubstituted amino and hydroxyl, and at least one of which substituents is protected with an enzymatically-removable protective group, (B) subjecting the bilirubin in the sample to coexist with ascorbate oxidase, the precursor of reaction promoter and an enzyme having the activity of removing the protective group from the substituent in the substituted aromatic hydrocarbon or substituted aromatic heterocyclic compound in an aqueous medium to thereby oxidize the bilirubin, (C) measuring a change in absorbance of the aqueous medium, and (D) comparing the change in absorbance with a calibration curve.

The present invention provides a reagent for quantitative determination of bilirubin, comprising ascorbate oxidase and a reaction promoter selected from the group consisting of a), b) and c):
  a) substituted aromatic hydrocarbon with at least two substituents which are independently selected from substituted amino, unsubstituted amino and hydroxyl,
  b) substituted aromatic heterocyclic compound with at least two substituents which are independently selected from substituted amino, unsubstituted amino and hydroxyl, and
  c) organic iron compound.

The present invention also provides a reagent for quantitative determination of bilirubin, comprising ascorbate oxidase, a precursor of reaction promoter selected from the group consisting of a) and b):
  a) substituted aromatic hydrocarbon with at least two substituents which are independently selected from substituted amino, unsubstituted amino and hydroxyl, and at least one of which substituents is protected with an enzymatically-removable protective group, and b) substituted aromatic heterocyclic compound with at least two substituents which are independently selected from substituted amino, unsubstituted amino and hydroxyl, and at least one of which substituents is protected with an enzymatically-removable protective group, and an enzyme having the activity of removing the protective group from the substituent in the substituted aromatic hydrocarbon or substituted aromatic heterocyclic compound.

DETAILED DESCRIPTION OF THE INVENTION

Figure 1:
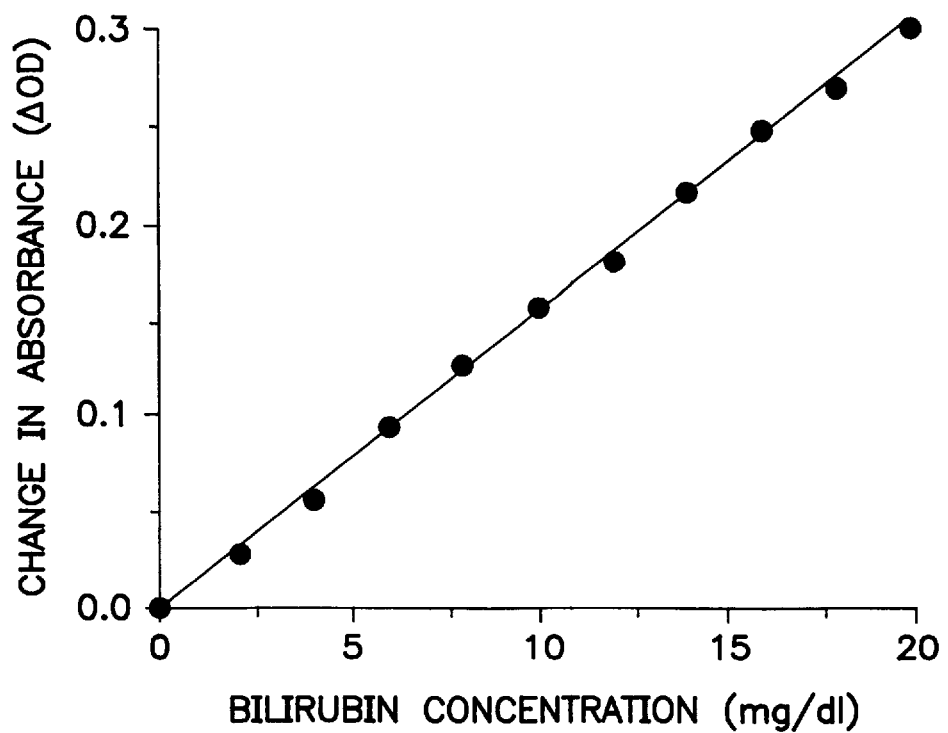
FIG. 1 shows a calibration curve of direct bilirubin.

The terminology "bilirubin" as referred to herein indicates any of indirect bilirubin, direct bilirubin and total bilirubin. The indirect bilirubin is free bilirubin ($C_{33}H_{36}N_4O_6$), while the direct bilirubin is a mono- or di-glucronide of indirect bilirubin. The total bilirubin is the sum of such indirect bilirubin and direct bilirubin.

The aqueous medium to be used in the present invention includes aqueous liquids such as buffers and physiological saline, and buffers are preferred.

Any and every known buffer can be used in the present invention, but buffers having different pH ranges shall be employed depending on the object for quantitatively determining direct bilirubin or total bilirubin. Precisely, according to the present invention, it is possible to differentially determine direct bilirubin and total bilirubin in a sample by controlling the pH value of the aqueous medium. The amount of indirect bilirubin in the sample can be calculated by subtracting the amount of direct bilirubin from the amount of total bilirubin. The concentration of the buffer to be used as the aqueous medium is preferably from 1 mM to 1M, more preferably from 10 to 200 mM.

To quantitatively determine direct bilirubin according to the present invention, preferably employed is a buffer having a pH of from 2.0 to 4.5, preferably from 2.5 to 4.0. For example, the buffer includes lactic acid buffer, citric acid buffer, acetic acid buffer, succinic acid buffer, glycine buffer, 3,3-dimethylglutaric acid buffer, etc.

In the pH range, direct bilirubin in a sample is oxidized but indirect bilirubin in the sample is not substantially oxidized. Therefore only the amount of direct bilirubin in the sample can be measured.

On the other hand, if total bilirubin is desired to be determined according to the present invention, employed is a buffer having a pH of from 5.0 to 12.0, preferably from 6.5 to 9.5. For example, the buffer includes lactic acid buffer, citric acid buffer, acetic acid buffer, succinic acid buffer, phthalic acid buffer, phosphoric acid buffer, triethanolamine buffer, diethanolamine buffer, boric acid buffer, glycine buffer, veronal-HCl buffer, tris(hydroxymethyl) aminomethane-HCl buffer, etc. Of these buffers, preferred are phosphoric acid buffer, triethanolamine buffer, diethanolamine buffer, boric acid buffer, glycine buffer, veronal-HCl buffer and tris(hydroxymethyl)aminomethane-HCl buffer.

In the pH range, both direct bilirubin and indirect bilirubin in a sample are substantially oxidized. Therefore the amount of total bilirubin in the sample can be measured.

Any and every bilirubin-containing sample that is miscible with an aqueous medium can be applied to the present invention. As examples, mentioned are biological fluid, such as plasma, serum, urine, etc.

Any and every ascorbate oxidase can be used in the present invention, including, for example, ascorbate oxidases derived from animals, vegetables and microorganisms and modified natural enzymes to be obtained through genetic engineering.

Regarding the activity of the enzyme, ascorbate oxidase, its activity to oxidize bilirubin is usually extremely poor and therefore the enzyme can not practical used in oxidation of bilirubin. However, its activity is extremely increased in the presence of a reaction promoter described hereinafter and therefore the enzyme can be used substantially for oxidizing bilirubin in the presence of the reaction promoter.

The concentration of ascorbate oxidase to be used in the present invention is preferably from 5 to 1000 U/ml, more preferably from 10 to 500 U/ml in the aqueous medium.

The reaction promoter to be used in the present invention includes the group consisting of a), b) and c):

a) substituted aromatic hydrocarbon with at least two substituents which are independently selected from substituted amino, unsubstituted amino and hydroxyl, b) substituted aromatic heterocyclic compound with at least two substituents which are independently selected from substituted amino, unsubstituted amino and hydroxyl, and c) organic iron compound.

The aromatic hydrocarbon includes, for example, benzene, naphthalene, anthracene, phenanthrene and pyrene. Of these compounds, preferred are benzene, naphthalene and anthracene;

and more preferred are benzene and naphthalene.

The aromatic heterocyclic compound may be nitrogen-containing aromatic heterocyclic compound, including, for example, pyridine, pyrazine, pyrimidine, pyridazine, quinoline, isoquinoline, quinoxaline, quinazoline, cinnoline, phthalazine, naphthyridine, indole and acridine. Preferred are pyridine, pyrazine, pyrimidine, pyridazine, quinoline, isoquinoline, quinoxaline, quinazoline, cinnoline, phthalazineandnaphthyridine; andmorepreferredarequinoline, isoquinoline, quinoxaline and quinazoline.

The substituted amino may have 1 or 2, same or different substituents which, for example, can be selected from substituted or unsubstituted alkyl, alkoxy, acyl, alkenyl, substituted or unsubstituted aryl, and substituted or unsubstituted aromatic heterocyclic group. Of these substituents, preferred is substituted or unsubstituted alkyl.

The alkyl moiety in the substituted or unsubstituted alkyl and the alkoxy may be linear or branched alkyl having from 1 to 10 carbon atoms, preferably from 1 to 6 carbon atoms, and includes, for example, methyl, ethyl, propyl, isopropyl, butyl, isobutyl, sec-butyl, tert-butyl, pentyl, neopentyl, hexyl, heptyl, octyl, nonyl and decyl.

The acyl may be linear or branched alkanoyl having from 1 to 6 carbon atoms which includes, for example, formyl, acetyl, propionyl, butyryl, isobutyryl, valeryl, isovaleryl and pivaloyl, or aroyl which includes, for example, benzoyl and naphthoyl.

The alkenyl may be linear or branched alkenyl having from 2 to 6 carbon atoms, which includes, for example, vinyl, allyl, 2-butenyl, 2-pentenyl and 2-hexenyl.

The substituted or unsubstituted aryl includes, for example, phenyl and naphthyl. The substituted or unsubstituted aromatic heterocyclic group includes, for example, pyridyl, pyrimidinyl, quinolyl, imidazolyl, triazolyl, furyl, thienyl, pyrazolyl, thiazolyl, oxazolyl and oxadiazolyl.

The substituted alkyl may have from 1 to 3, same or different substituents which, for example, can be selected from alkoxy, acyl, aryl, hydroxyl, carboxyl, sulfo, phospho, and halogen. These alkoxy, acyl and aryl may have the same meanings as those mentioned hereinabove, and the halogen includes fluorine, chlorine, bromine and iodine.

The substituted aryl and the substituted aromatic heterocyclic group each may have from 1 to 3, same or different substituents which, for example, can be selected from alkyl, alkoxy, acyl, halogen, carboxyl, alkoxycarbonyl, cyano and amino. The alkyl, alkoxy, acyl and halogen may have the same meanings as those mentioned hereinabove, and the alkyl moiety in the alkoxycarbonyl may have the same meaning as the alkyl also mentioned hereinabove.

The substituted aromatic hydrocarbon and the substituted aromatic heterocyclic compound which can be used as the reaction promoter in the present invention may optionally be substituted by additional substituents, in addition to the above-mentioned, at least two substituents which are independently selected from substituted amino, unsubstituted amino and hydroxy. The additional substituents can be from 1 to 4 substituents which are independently selected from halogen and substituted or unsubstituted alkyl. The halogen and the substituted or unsubstituted alkyl may have the same meanings as those mentioned hereinabove.

The organic iron compound which can be also be as the reaction promoter in the present invention may include, for example, hexacyanoferrate, substituted or unsubstituted ferrocene and iron chelate.

Hexacyanoferrate includes hexacyanoferrate (II) and hexacyanoferrate(III). The base that forms the salts includes, for example, ammonium ion and metal ion. The metal ion includes, for example, alkali metal ion such as lithium, sodium and potassium ion; alkaline earth metal ion such as magnesium and calcium ion; and also aluminium and zinc ion.

The substituents for the substituted ferrocene may include, for example, acyl and substituted or unsubstituted alkyl. The acyl and the substituted or unsubstituted alkyl have the same meanings as those mentioned hereinabove.

Iron chelate shall result from the bonding of an iron element to a chelating compound. Any known chelating compound capable of coordinating with an iron element can be used to form such iron chelate for use in the present invention. As examples, mentioned are porphyrin, polyaminocarboxylic acid and hydroxycarboxylic acid.

Especially preferred examples of the reaction promoter are compounds of the following general formula (I):

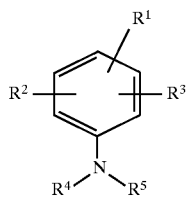

(I)

wherein $R^1$ represents hydroxyl, or substituted or unsubstituted amino; $R^2$ and $R^3$ may be the same or different, and each represents hydrogen, halogen, or substituted or unsubstituted alkyl; $R^4$ and $R^5$ may be the same or different, and each represents hydrogen, or substituted or unsubstituted alkyl;

and compounds of the following general formula (II):

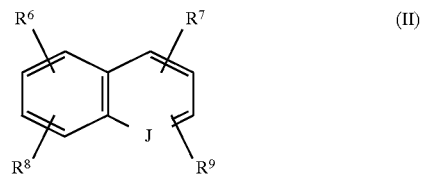

(II)

wherein $R^6$, $R^7$, $R^8$ and $R^9$ may be the same or different, and at least two of the $R^6$, $R^7$, $R^8$ and $R^9$ are independently selected from substituted amino, unsubstituted amino and hydroxyl, and the remains are independently selected from hydrogen, halogen, hydroxyl, substituted amino, unsubstituted amino, substituted alkyl and unsubstituted alkyl; J represents CH or N.

The halogen, the substituted or unsubstituted amino, and the substituted or unsubstituted alkyl may have the same meanings as those mentioned hereinabove.

Specific examples of the reaction promoter for use in the present invention are mentioned below.

Examples of aromatic hydrocarbon having a benzene ring include 4-amino-2,6-dibromophenol, 2,6-dibromo-4-methylaminophenol, 2,6-dibromo-4-dimethylaminophenol, 2,6-dibromo-4-sulfopropylaminophenol, 4-amino-2,6-dichlorophenol, 2,6-dichloro-4-methylaminophenol, 2,6-dichloro-4-dimethylaminophenol, 2,6-dichloro-4-sulfopropylaminophenol, 4-amino-2,6-diiodophenol, 2,6-diiodo-4-methylaminophenol, 2,6-diiodo-4-dimethylaminophenol, 2,6-diiodo-4-sulfopropylaminophenol, 4,5-dimethyl-1,2-phenylenediamine, 2,5-dimethyl-1,4-phenylenediamine, 4,5-diethyl-1,2-phenylenediamine, 2,5-diethyl-1,4-phenylenediamine, N,N-dimethyl-1,4-phenylenediamine, and N,N-diethyl-1,4-phenylenediamine.

Examples of aromatic hydrocarbon having a naphthalene ring include 1,4-naphthol, 1,6-naphthol, 4-amino-1-naphthol, 5-amino-1-naphthol, and 1-amino-2-naphthol.

Examples of aromatic heterocyclic compound having a quinoline ring include 5-amino-8-hydroxyquinoline, 5,8-diaminoquinoline, and 5,8-dihydroxyquinoline.

Examples of organic iron compound include hexacyanoferrate such as potassium ferrocyanide, sodium ferrocyanide, magnesium ferrocyanide, ammonium ferrocyanide, potassium ferricyanide, sodium ferricyanide, magnesium ferricyanide, and ammonium ferricyanide; and ferrocene such as ferrocene, ferrocene-dicarboxylic acid, and ferrocenylmethanol. As examples of iron chelate, mentioned are iron polyaminocarboxylate chelate such as iron ethylenediaminetetraacetate, and ethylene glycol bis(2-aminoethyl ether)-tetraacetate/iron(III); and iron oxycarboxylate chelate such as iron glycolate, iron glycerate, iron lactate, iron malate, iron citrate, and iron tartrate.

The concentration of the reaction promoter to be used in the present invention is preferable from 1 to 1000 $\mu$M, more preferably from 10 to 200 $\mu$M in the aqueous medium.

The precursor of reaction promoter to be used in the present invention includes the group consisting of a) and b)
  a) substituted aromatic hydrocarbon with at least two substituents which are independently selected from substituted amino, unsubstituted amino and hydroxyl, and at least one of which substituents is protected with an enzymatically-removable protective group, and
  b) substituted aromatic heterocyclic compound with at least two substituents which are independently selected from substituted amino, unsubstituted amino and hydroxyl, and at least one of which substituents is protected with an enzymatically-removable protective group.

The substituted aromatic hydrocarbon and the substituted aromatic heterocyclic compound with at least two substituents which are independently selected form substituted amino, unsubstituted amino and hydroxyl may have the same meanings as those mentioned hereinabove except that at least one of the substituted amino have only 1 substituent provided that both of the substituents are substituted amino.

The enzymatically-removable protective group includes, for example, amino acid residues for the substituted or unsubstituted amino substituent; and, for example, saccharide residues, phospho and sulfo for the hydroxyl substituent.

The amino acid residues may be derived from any amino acids but preferably from α-amino acids, which include, for example, glycine, alanine, valine, leucine, isoleucine, serine, threonine, aspartic acid, glutamic acid, lysine, hydroxylysine, arginine, cysteine and methionine.

The saccharide residue may be derived from any saccharide but preferably from mono-saccharides, of which the number of carbon atoms is not specifically defined provided that it is hydrolyzable with enzyme. Preferred are pentose and hexose; and more preferred are hexose, such as galactose, glucose, talose, mannose, sorbose, tagatose, fructose and psicose.

The substituted aromatic hydrocarbon and the substituted aromatic heterocyclic compound which can be used as the precursor of reaction promoter in the present invention may optionally substituted by additional substituents in addition to the above-mentioned, at least two substituents which are independently selected from substituted amino, unsubstituted amino and hydroxy, and at least one of which substituents is protected with an enzymatically-removable protective group. The additional substituents can be from 1 to 4 substituents which are independently selected from halogen and substituted or unsubstituted alkyl. The halogen and the substituted or unsubstituted alkyl may have the same meaning those mentioned hereinabove.

Especially preferred examples of the precursor of reaction promoter are compounds of the following general formula (III):

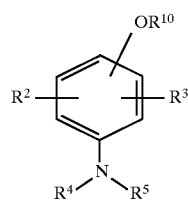

wherein $R^{10}$ represents a saccharide residue; and $R^2$, $R^3$, $R^4$ and $R^5$ have the same meanings as those mentioned hereinabove;

and compounds of the following general formula (IV):

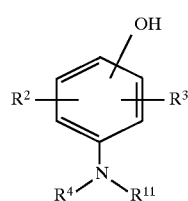

wherein $R^{11}$ represents an amino acid residue; and $R^2$, $R^3$ and $R^4$ have the same meanings as those mentioned hereinabove.

The saccharide residue and the amino acid residue have the same meanings as those mentioned hereinabove.

Specific examples of the precursor of reaction promoter as protected with a saccharide residue are 4-amino-2,6-dichlorophenol-β-D-galactopyranoside, 4-amino-2,6-dichlorophenol-β-D-glucopyranoside, 4-amino-2,6-dichlorophenol-β-D-mannopyranoside, 2,6-dichloro-4-methylaminophenol-β-D-galactopyranoside, 2,6-dichloro-4-dimethylaminophenol-β-D-galactopyranoside, and 2,6-dichloro-4-sulfopropylaminophenol-β-D-galactopyranoside; and those of the precursor of reaction promoter as protected with an amino acid residue are 2,6-dibromo-4-(N-leucyl)aminophenol, and 2,6-dibromo-4-(N-γ-glutamyl)aminophenol.

The concentration of the precursor of reaction promoter to be used in the present invention is preferably from 1 to 1000 μM, more preferably from 10 to 200 μM in the aqueous medium.

The enzyme having the activity of removing the protective group from the substituent in the substituted aromatic hydrocarbon or substituted aromatic heterocyclic compound includes, for example, any hydrolase and transferase can be used depending on the type of the enzymatically-removable protective group to be removed. For example, to remove the protective group from the precursor of reaction promoter, β-galactosidase can be applied to 4-amino-2,6-dichlorophenol with the hydroxyl being protected with a β-D-galactosyl group; leucine aminopeptidase can be applied to 4-amino-2,6-dibromophenol with the amino being protected with a leucine group; and γglutamyl transpeptidase can be applied to 4-amino-2,6-dichlorophenol with the amino being protected with a γ-glutamic acid residue. When transferase such as γ-glutamyl transpeptidase is applied to the precursor of reaction promoter, it is desirable to add thereto a receptor such as glycylglycine.

The concentration of the enzyme having the activity of removing the protective groups from the substituent in the substituted aromatic hydrocarbon or substituted aromatic heterocyclic compound to be used in the present invention is preferably from 0.1 to 500 U/ml, more preferably from 1 to 100 U/ml in the aqueous medium.

The concentration of the receptor is preferably from 1 to 100 mM in the aqueous medium.

It is desirable that the precursor of reaction promoter is decomposed by the enzyme having the activity of removing the protective group just before or simultaneously with the oxidation of bilirubin by ascorbate oxidase in the present invention.

After having been decomposed with the enzyme having the activity of removing the protective group, the precursor of reaction promoter is converted into the reaction promoter of any of the above-mentioned, namely the reaction promoter selected from the group consisting of a) and b):

a) substituted aromatic hydrocarbon with at least two substituents which are independently selected from substituted amino, unsubstituted amino and hydroxyl, and b) substituted aromatic heterocyclic compound with at least two substituents which are independently selected from substituted amino, unsubstituted amino and hydroxyl.

In the presence of the reaction promoter thus formed, it is possible to determine the amount of bilirubin in a sample according to the method of the present invention.

The precursor of reaction promoter, as having been protected with an enzymatically-removable protective group, hardly undergoes change, for example, through spontaneous oxidative decomposition in an aqueous solution, and its stability in the reagent composition of the present invention can be kept high especially in an aqueous solution. The precursor of reaction promoter itself does not promote the oxidation of bilirubin with ascorbate oxidase but, after having been decomposed with an enzyme having the activity of removing the protective group, it is converted into the reaction promoter capable of promoting the oxidation for itself.

The method of the present invention is carried out by subjecting the bilirubin in the sample to coexist with ascorbate oxidase and the reaction promoter in an aqueous medium to thereby oxidize the bilirubin, measuring a change in absorbance of the aqueous medium, and comparing the change in absorbance with a calibration curve.

The reaction of bilirubin oxidation is carried out by adding the reaction promoter, a sample containing bilirubin and optionally a surfactant for preventing cloudness of the sample to an aqueous medium, preincubating the resulting the aqueous medium at 20° to 50° C. for 0 to 15 minutes, usually at 37° C. for 5 minutes, adding ascorbate oxidase to the aqueous medium, and incubating the aqueous medium thus formed at 20° to 50° C. for 3 to 15 minutes, usually at 37° C. for 5 minutes Further the method of the present invention is preferably carried out by subjecting the bilirubin in the sample to coexist with ascorbate oxidase, the precursor of reaction promoter and an enzyme having the activity of removing the protective group from the substituent in the substituted aromatic hydrocarbon or substituted aromatic heterocyclic compound in an aqueous medium to thereby oxidize the bilirubin, measuring a change in absorbance of the aqueous medium, and comparing the change in absorbance with a calibration curve.

The reaction of bilirubin oxidation is carried out by adding the precursor of reaction promoter, a sample containing bilirubin and optionally a surfactant for preventing cloudness of the sample to an aqueous medium, preincubating the resulting aqueous medium at 20° to 50° C. for 0 to 15 minutes, usually at 37° C. for 5 minutes, adding ascorbate oxidase and an enzyme having the activity of removing the protective group to the aqueous medium, and incubating the aqueous medium thus formed at 20° to 50° C. for 3 to 15 minutes, usually at 37° C. for 5 minutes.

Examples of the surfactant are Triton X-100, and sodium dodecylsulfate (SDS).

The change in absorbance of the aqueous medium was caused by changing the bilirubin to biliverdin ($C_{33}H_{34}N_4O_6$).

To optically determine the quantitative change in absorbance in the method of the present invention, it is desirable that the decrease in bilirubin is determined through the measurement of the decrease in the absorbance of the aqueous medium at from 440 to 470 nm while the increase in biliverdin is determined through the measurement of the increase in the absorbance of the aqueous medium at 330 nm or 380 nm.

The measured change in absorbance are plotted against the corresponding concentrations of bilirubin to construct calibration curve representing the relationship therebetween. Then bilirubin concentration of sample is calculated by comparing the measured change in absorbance with the calibration curve.

To measure the amount of total bilirubin in a sample according to the present invention, it is possible to add to the aqueous medium an activating reagent of diazoation of indirect bilirubin being selected from, for example, surfactant, aromatic carboxylic acid, sulfa drug and alcohol. The surfactant is preferably anionic surfactant, such as cholic acid and dodecylsulfuric acid. The aromatic carboxylic acid includes, for example, benzoic acid, phthalic acid and salicylic acid. The sulfa drug includes, for example, sulfanilamide, sulfamerazine, sulfisoxazole, sulfathiazole, and sulfaguanidine. The alcohol may have from 1 to 6 carbon atoms and includes, for example, methanol, ethanol, propanol, isopropanol, butanol, pentanol and hexanol.

The surfactant, aromatic carboxylic acid and sulfa drug can be used in the form of the salt with a base. The base includes, for example, alkali metal ion such as lithium, sodium and potassium ion, alkaline earth metal ion such as magnesium and calcium ion, and also aluminium and zinc ion.

The concentration of the activating reagent capable of activating indirect bilirubin, if added, in the reaction solution is preferably from 0 to 5%, more preferably from 0.1 to 1% in the aqueous medium.

The reagent for quantitative determination of bilirubin of the present invention comprises ascorbate oxidase and a reaction promoter. There agent for quantitative determination of bilirubin of the present invention may be in the form of a kit comprising:

1) a reagent comprising ascorbate oxidase, and 2) a reagent comprising a reaction promoter.

Also the reagent for quantitative determination of bilirubin of the present invention comprises ascorbate oxidase, a precursor of reaction promoter, and an enzyme having the activity of removing the protective group from the substituent in the substituted aromatic hydrocarbon or substituted aromatic heterocyclic compound.

The reagent for quantitative determination of bilirubin of the present invention may be in the form of a kit comprising:

1) a reagent comprising ascorbate oxidase, 2) a reagent comprising a precursor of reaction promoter, and 3) a reagent comprising an enzyme having the activity of removing the protective group from the substituent in the substituted aromatic hydrocarbon or substituted aromatic heterocyclic compound.

The reagent for quantitative determination of bilirubin of the present invention also may be in the form of a kit comprising:

1) a reagent comprising ascorbate oxidase and a precursor of reaction promoter, and 2) a reagent comprising an enzyme having the activity of removing the protective group from the substituent in the substituted aromatic hydrocarbon or substituted aromatic heterocyclic compound.

The reagent for quantitative determination of bilirubin of the present invention also may be in the form of a kit comprising:

1) a reagent comprising a precursor of reaction promoter and 2) a reagent comprising ascorbate oxidase and an enzyme having the activity of removing the protective group from the substituent in the substituted aromatic hydrocarbon or substituted aromatic heterocyclic compound.

Preferably each reagent in a kit further comprising an aqueous medium, preferably a buffer.

From the viewpoint of differential determination of bilirubin, the reagent for quantitative determination of direct bilirubin is preferably in the form of a kit comprising:

1) a buffer having the pH of from 2.0 to 4.5 comprising a precursor of reaction promoter (referred to as promoter reagent), 2) a buffer comprising ascorbate oxidase and an enzyme having the activity of removing the protective group from the substituent in the substituted aromatic hydrocarbon or substituted aromatic heterocyclic compound (referred to as enzyme reagent), and the reagent for quantitative determination of total bilirubin is preferably in the form of a kit comprising:

1) a buffer having the pH of from 5.0 to 12.0 comprising a precursor of reaction promoter and optionally an activating reagent of diazoation of indirect bilirubin (referred to as promoter reagent),
2) a buffer comprising ascorbate oxidase and an enzyme having the activity of removing the protective group from the substituent in the substituted aromatic hydrocarbon or substituted aromatic heterocyclic compound (referred to as enzyme reagent).

It is desirable that the pH of the enzyme reagent is determined in consideration of the stability of the enzyme in its solution; while it is desirable that the pH of the promoter reagent is so controlled that, after the enzyme reagent is added to the promoter reagent, it maybe a desired pH value to determine the bilirubin.

The above-mentioned compounds and enzymes are commercially available. For example, they are described in catalogs of chemical reagents as published by Tokyo Kasei KK, Dojin Kagaku Kenkyu-jo KK, Wako Jun-yaku Kogyo KK, Seishin KK, Nakarai KK and Aldrich Co.

TEST EXAMPLE 1

0.1 ml of a bilirubin sample containing 15 mg/dl of Interference Check-A Bilirubin-C produced by Kokusai Shiyaku KK (this is hereinafter referred to as "direct bilirubin reagent"), 2.2 ml of 0.1M lactic acid buffer (pH 3.5), and 0.05 ml of a solution containing 3.1 mM of the reaction promoter as shown in Table 1 below were mixed and preincubated at 37° C. for 5 minutes. The absorbance of the resulting mixture at 450 nm was measured with an auto-recording spectrophotometer, Hitachi's U-3210 Model (absorbance before reaction: $A_0$).

Next, 0.75 ml of 10 mM potassiumphosphate buffer (pH 6.0) containing 400 U/ml of ascorbate oxidase (derived from *Acremonium sp.*, produced by Asahi Kasei Kogyo KK) was added to the mixture and reacted at 37° C. for 5 minutes, and the absorbance of the thus-reacted mixture was measured (absorbance after reaction: $A_2$). The wording "change in absorbance before and after reaction" as will be referred to, as the case may be hereinafter as the simplewording "change in absorbance", which indicates the difference between $A_1$ and $A_2$, and $A_1$ is derived from $A_0$ by correcting the amount of the liquid before the reaction into the amount of the liquid after the reaction. The results obtained are shown in Table 1. From the data, it is evident that, bilirubin was oxidized by ascorbate oxidase with the present reaction promoter, while bilirubin was not almost oxidized by ascorbate oxidase with any of the known reaction promoters tested as well as the case with no reaction promoter.

TABLE 1

| Reaction Promoter | Change in Absorbance |
| --- | --- |
| None | 0.030 |
| 4-Amino-2,6-dibromophenol | 0.191 |
| 2,6-Dibromo-4-methylaminophenol | 0.191 |
| 2,6-Dibromo-4-dimethylaminophenol | 0.201 |
| 2,6-Dibromo-4-sulfopropylaminophenol | 0.196 |
| 2,6-Dichloro-4-dimethylaminophenol | 0.206 |
| 4,5-Dimethyl-1,2-phenylenediamine | 0.095 |

TABLE 1-continued

| Reaction Promoter | Change in Absorbance |
| --- | --- |
| 2,5-Dimethyl-1,4-phenylenediamine | 0.167 |
| N,N-Dimethyl-1,4-phenylenediamine | 0.048 |
| N,N-Diethyl-1,4-phenylenediamine | 0.154 |
| 1,6-Naphthol | 0.064 |
| 4-Amino-1-naphthol | 0.080 |
| 5-Amino-1-naphthol | 0.049 |
| 5-Amino-8-hydroxyquinoline | 0.105 |
| Potassium Ferrocyanide | 0.195 |
| Sodium Ferrocyanide | 0.047 |
| Iron(III) Ethylenediaminetetraacetate | 0.045 |
| 1,1'-Ferrocene-dicarboxylic Acid | 0.138 |
| Known Reaction Promoters | |
| Sodium Salicylate | 0.030 |
| Sulfosalicylic Acid | 0.031 |
| Sodium Dodecylsulfate | 0.029 |
| Sulfanilamide | 0.028 |

TEST EXAMPLE 2

In the same manner as in Test Example 1, except that any of the precursor of reaction promoters shown in Table 2 below was used in place of the reaction promoters used in Test Example 1, the reaction mixture was preincubated and the absorbance of the reaction solution before reaction was measured. Next, 0.75 ml of 10 mM potassium phosphate buffer (pH 6.0) containing 400 U/ml of ascorbate oxidase and 10 U/ml of β-galactosidase (derived from *Asergillus sp.*, produced by Toyo Boseki KK) was added to the reaction solution and reacted in the same manner as in Test Example 1, and the absorbance of the thus-reacted reaction solution was measured. Then, the change in absorbance before and after reaction was obtained. The results are shown in Table 2. When β-galactosidase was not added to the reaction solution (no enzyme), there was almost no difference in the change of absorbance between the reaction solution containing the precursor of reaction promoter and that without containing β-galactosidase. Therefore, it is understood that the precursor of reaction promoter does not promote the oxidation of the bilirubin but the precursor of reaction promoter may change into the reaction promoter by being hydrolyzed with β-galactosidase.

TABLE 2

| | Change in Absorbance | |
| --- | --- | --- |
| Precursor of Reaction Promoter | No Enzyme | β-galactosi-dase |
| 4-Amino-2,6-dichlorophenol-β-D-galactopyranoside | 0.030 | 0.214 |
| 2,6-Dichloro-4-methylaminophenol-β-D-galactopyranoside | 0.031 | 0.232 |
| 2,6-Dichloro-4-dimethylaminophenol-β-D-galactopyranoside | 0.029 | 0.223 |
| 2,6-Dichloro-4-sulfopropylaminophenol-β-D-galactopyranoside | 0.029 | 0.223 |

TEST EXAMPLE 3

The precursor of reaction promoter as shown in Table 3 below was tested in the same manner as in Test Example 2, except that piperazine-1,4-bis(2-hydroxy-3-propane) sulfonic acid (hereinafter referred to as POPSO) buffer (pH 8.0) was used in place of 0.1M potassium phosphate buffer, that 10 U/ml of γ-glutamyl transferase (derived from *Bacillus subtilis*, produced by Kyowa Hakko Kogyo KK) was used in place of β-galactosidase, and that 20 mM glycylglycine was added to the reaction solution. The results are shown in Table 3. When γ-glutamyl transferase was not added to the reaction solution (no enzyme), there was almost no difference in the change in absorbance between the reaction solution containing the precursor of reaction promoter and that without containing the promoter. Therefore, it is understood that the precursor of reaction promoter tested herein does not promote by itself the oxidation of the bilirubin but is hydrolyzed by γ-glutamyl transferase into the corresponding, active reaction promoter.

TABLE 3

| Precursor of Reaction Promoter | Change in Absorbance | |
|---|---|---|
| | No Enzyme | γ-glutamyl transferase |
| 2,6-Dibromo-4-(N-γ-glutamyl)aminophenol | 0.032 | 0.209 |

TEST EXAMPLE 4

5 mM of the compound shown in Table 4 below was dissolved in 0.1M lactic acid buffer (pH 3.5) and 0.1M POPSO buffer (pH 8.0) and the solution was put into a brown reagent bottle. The bottle was stored at 30° C., whereupon the color of the solution therein was observed with the naked eye. It was found that the solution of 4-amino-2,6-dibromophenol was colorless and transparent just after its preparation but became reddish-brown after having been stored long. On the other hand, the solution of 4-amino-2, 6-dichlorophenol-β-D-galactopyranoside and that of 2,6-dibromo-4-(N-γ-glutamyl) aminophenol kept colorless and transparent while being stored for 14 days. The results are shown in Table 4.

TABLE 4

| Compound | pH | Duration of Storage | |
|---|---|---|---|
| | | 0 day | 14 days |
| 4-Amino-2,6-dibromo-phenol | 3.5 | − | + |
| | 8.0 | − | ++ |
| 4-Amino-2,6-dichloro-phenol-β-D-galactopyranoside | 3.5 | − | − |
| | 8.0 | − | − |
| 2,6-Dibromo-4-(N-γ-glutamyl)aminophenol | 3.5 | − | − |
| | 8.0 | − | − |

−: Colorless and transparent
+: Light reddish-brown
++: Reddish-brown

TEST EXAMPLE 5

A bilirubin sample comprising 15 mg/dl of direct bilirubin, ditaurobilirubin (produced by Porphyrin Products Inc.) was tested in the same manner as in Test Example 1, except that 2.2 ml of a buffer having a varying pH was used in place of 0.1M lactic acid buffer (pH 3.5) and that 0.05 ml of 3.1 mM 4-amino-2,6-dibromophenol was used as the reaction promoter. Precisely, citric acid buffer was used in preparing reaction solution having varying pH values of from 2.5 to 5.0; phosphoric acid buffer was used in preparing reaction solution having varying pH values of from 5.5 to 7.0; and tris(hydroxymethyl)aminomethane-HCl buffer was used in preparing reaction solution having varying pH values of from 7.5 to 9.0. When 10 mM potassium phosphate buffer (pH 6.0) containing ascorbate oxidase was added to the reaction solution, the pH values of the reaction solution did not almost vary. The results are shown in Table 5 below. The direct bilirubin gave the change in absorbance to almost the same degree in any of the buffers having such varying pH values.

TABLE 5

| pH of Reaction solution | Change in Absorbance |
|---|---|
| 2.0 | 0.175 |
| 2.5 | 0.175 |
| 3.0 | 0.178 |
| 3.5 | 0.180 |
| 4.0 | 0.182 |
| 4.5 | 0.179 |
| 5.0 | 0.180 |
| 5.5 | 0.171 |
| 6.0 | 0.181 |
| 6.5 | 0.179 |
| 7.0 | 0.180 |
| 7.5 | 0.180 |
| 8.0 | 0.180 |
| 8.5 | 0.178 |
| 9.0 | 0.175 |
| 9.5 | 0.180 |

TEST EXAMPLE 6

0.1 ml of a bilirubin sample containing 30 mg/dl of Interference Check-A Bilirubin-F produced by Kokusai Shiyaku KK (this is hereinafter referred to as "indirect bilirubin reagent") was tested in the same manner as in Test Example 5 [SDS-free, this is referred to in Table 6 below as SDS(−)]. Apart from this, the same sample was tested in the same manner, except that SDS was added at 0.1% to the 0.1M buffer having various pH values [SDS added, this is referred to in Table 6 below as SDS (+) ]. The results are shown in Table 6. Under the condition of a pH 4.0 or lower and SDS (−), there was found almost no change in absorbance of the reaction solution containing the indirect bilirubin, but was found some change in absorbance of the SDS(−) reaction solution having a pH of 4.5 or higher. It is known that the indirect bilirubin was not substantially oxidized in the SDS(−) reaction solution under the condition of pH 4.5 or lower. On the other hand, there was found a maximum change in absorbance in the SDS(+) reaction solution having a pH of 7.0 or higher. It is known that the indirect bilirubin was completely oxidized in the SDS(+) reaction solution under the condition of pH 7.0 or higher.

TABLE 6

| pH of Reaction solution | Change in Absorbance | |
|---|---|---|
| | SDS(−) | SDS(+) |
| 2.0 | 0.000 | 0.035 |
| 2.5 | 0.000 | 0.059 |
| 3.0 | 0.000 | 0.089 |
| 3.5 | 0.001 | 0.118 |
| 4.0 | 0.012 | 0.154 |
| 4.5 | 0.059 | 0.213 |
| 5.0 | 0.142 | 0.260 |
| 5.5 | 0.189 | 0.296 |
| 6.0 | 0.237 | 0.325 |
| 6.5 | 0.260 | 0.343 |
| 7.0 | 0.284 | 0.349 |

TABLE 6-continued

| pH of Reaction solution | Change in Absorbance | |
|---|---|---|
| | SDS(−) | SDS(+) |
| 7.5 | 0.296 | 0.355 |
| 8.0 | 0.308 | 0.355 |
| 8.5 | 0.320 | 0.355 |
| 9.0 | 0.320 | 0.355 |
| 9.5 | 0.320 | 0.355 |

EXAMPLE 1

Direct bilirubin, ditaurobilirubin was dissolved into distilled water to prepare standard solutions for a calibration curve of bilirubin. The standard solutions have varying concentrations of 2, 4, 6, 8, 10, 12, 14, 16, 18 and 20 mg/dl.

0.1 ml of any of the standard solutions was added to 2.8 ml of 0.1M lactate buffer (pH 3.7) containing 54.2 μM of 4-amino-2,6-dibromophenol, and preincubated at 37° C. for 5 minutes. Next, 0.1 ml of 10 mM potassium phosphate buffer (pH 6.0) containing 1550 U/ml of ascorbate oxidase was added thereto and reacted at 37° C. for 5 minutes. The change in absorbance at 450 nm was obtained in each reaction solution comprising any of the standard solutions having such varying bilirubin contents. The data were plotted to give the calibration curve shown in FIG. 1. As shown in FIG. 1, the plotting of the data indicating the relationship between the bilirubin concentration and the change in absorbance gave a straight line that starts from the origin of the coordinate axes. Using this, therefore, it is possible to quantitatively determine the direct bilirubin.

EXAMPLE 2

Figure 2:
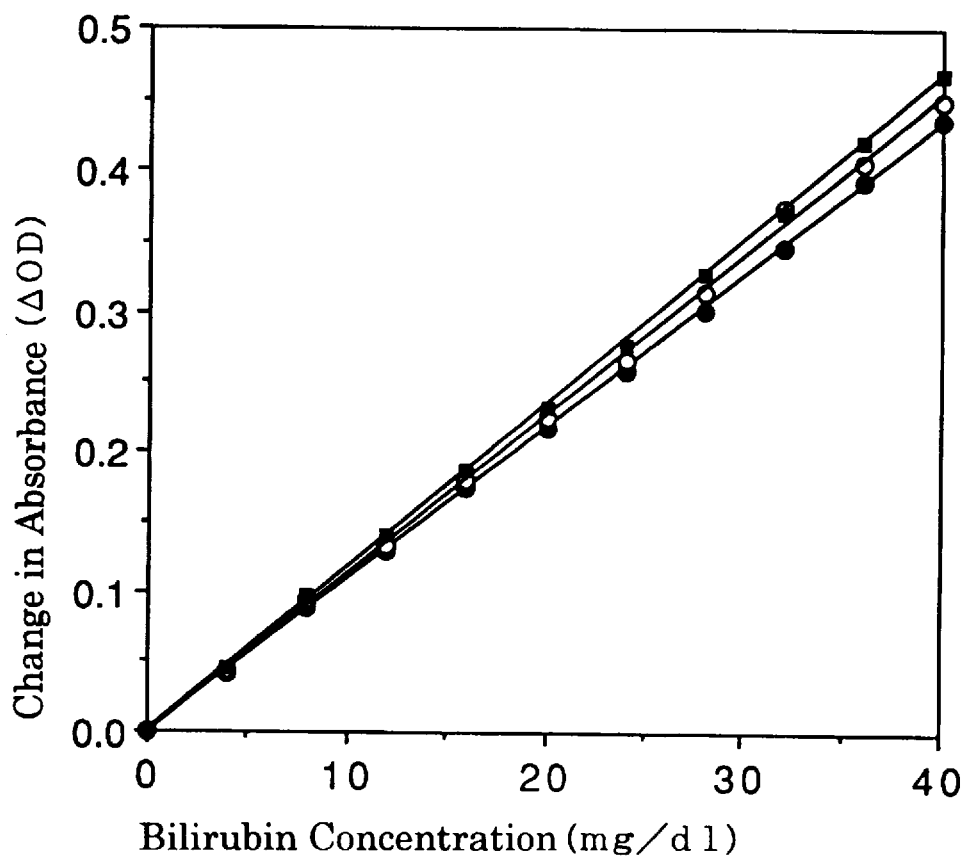
FIG. 2 shows calibration curves of total bilirubin, in which the line of -●- results from direct bilirubin, the line of -■- from indirect bilirubin, and the line of -○- from a 1:1 mixture of direct bilirubin and indirect bilirubin.

Using reagent of direct bilirubin, indirect bilirubin reagent, and a 1:1 mixture of the two, standard solutions for bilirubin calibration curves were prepared. The solutions have varying total bilirubin concentrations of 4, 8, 12, 16, 20, 24, 28, 32, 36 and 40 mg/dl in each bilirubin reagent. 0.1 ml of any of the standard solutions was added to 2.8 ml of 0.1M POPSO buffer (pH 8.0) containing 54.2 μM 4-amino-2,6-dibromophenol and 0.1% SDS, and preincubated at 37° C. for 5 minutes. Next, 0.1 ml of 10 mM POPSO buffer (pH 8.0) containing 1550 U/ml of ascorbate oxidase was added thereto and reacted at 37° C. for 5 minutes. The change in absorbance at 450 nm was obtained in each reaction solution comprising any of the standard solutions having such varying total bilirubin contents. The data were plotted to give the calibration curves shown in FIG. 2. As shown in FIG. 2, the plotting of the data of all the standard solutions containing any of direct bilirubin, indirect bilirubin and their mixture, the data indicating the relationship between the total bilirubin concentration and the change in absorbance, gave straight lines that start from the origin of the coordinate axes in each bilirubin reagent, and these three lines all incline upward similarly. The data obtained herein thus verify that any bilirubin, irrespective of its type, can be quantitatively determined in terms of the total bilirubin concentration.

EXAMPLE 3

Herein used was a serum sample, of which the direct bilirubin content had been measured to be 2.95 mg/dl using a direct bilirubin measuring kit (Direct Bilirubin II-HA Test Wako, produced by Wako Jun-yaku Kogyo KK) and of which the total bilirubin content had been measured to be 4.85 mg/dl using a total bilirubin measuring kit (Total Bilirubin II-HA Test Wako, produced by Wako Jun-yaku Kogyo KK).

The change in absorbance of the serum sample for direct bilirubin was obtained according to the method of Example 1, and that for total bilirubin was obtained according to the method of Example 2. In addition, the change in absorbance of each of two control samples having known bilirubin concentrations was obtained in the same manner. From the data thus obtained, the direct bilirubin concentration and the total bilirubin concentration in the serum sample were obtained according to the following equation (1). Briefly, one control sample was a direct bilirubin reagent having a known direct bilirubin concentration, and this was processed in the same manner as in Example 1; while the other control sample was a 1:1 mixture of a direct bilirubin reagent and an indirect bilirubin having a known total bilirubin concentration, and this was processed in the same manner as in Example 2. The results obtained are shown in Table 7 below.

$$\text{Bilirubin Concentration} = (A \times C)/B \quad (1)$$

where;

A is the change in absorbance of the serum sample,

B is the change in absorbance of the control sample,

C is the bilirubin concentration in the control sample (mg/dl).

TABLE 7

| Reaction Promoter | Direct Bilirubin (mg/dl) | Total Bilirubin (mg/dl) |
|---|---|---|
| 4-Amino-2,6-dibromophenol | 3.01 | 4.80 |
| 2,6-Dibromo-4-methylaminophenol | 3.05 | 4.75 |
| 2,6-Dibromo-4-dimethylaminophenol | 3.02 | 4.78 |
| 2,6-Dibromo-4-sulfopropylaminophenol | 3.01 | 4.85 |
| 2,6-Dichloro-4-dimethylaminophenol | 3.01 | 4.81 |
| 4,5-Dimethyl-1,2-phenylenediamine | 2.99 | 4.78 |
| 2,5-Dimethyl-1,4-phenylenediamine | 3.05 | 4.76 |
| N,N-Dimethyl-1,4-phenylenediamine | 3.06 | 4.83 |
| N,N-Diethyl-1,4-phenylenediamine | 3.00 | 4.77 |
| 1,6-Naphthol | 2.98 | 4.79 |
| 4-Amino-1-naphthol | 2.98 | 4.81 |
| 5-Amino-1-naphthol | 3.02 | 4.77 |
| 5-Amino-8-hydroxyquinoline | 2.98 | 4.82 |
| Potassium Ferrocyanide | 3.07 | 4.80 |
| Sodium Ferrocyanide | 3.05 | 4.76 |
| Iron(III) Ethylenediaminetetraacetate | 3.07 | 4.78 |
| 1,1'-Ferrocene-dicarboxylic Acid | 3.01 | 4.78 |

EXAMPLE 4

The same serum sample as in Example 3 was tested in the same manner as in Test Example 2 to obtain the change in absorbance of the sample for direct bilirubin therein. In addition, a control sample having a known bilirubin concentration was tested in the same manner to obtain the change in absorbance of the control sample. From the data thus obtained, the direct bilirubin concentration in the serum sample was obtained according to the above-mentioned equation (1). Briefly, the control sample used herein was a direct bilirubin reagent having a known bilirubin concentration. The results obtained are shown in Table 8 below.

TABLE 8

| Precursor of Reaction Promoter | Direct Bilirubin (mg/dl) |
| --- | --- |
| 4-Amino-2,6-dichlorophenol-β-D-galactopyranoside | 3.01 |
| 2,6-Dichloro-4-methylaminophenol-β-D-galactopyranoside | 3.09 |
| 2,6-Dichloro-4-dimethylaminophenol-β-D-galactopyranoside | 3.05 |
| 2,6-Dichloro-4-sulfopropylaminophenol-β-D-galactopyranoside | 3.11 |

EXAMPLE 5

The same serum sample as in Example 3 was tested in the same manner as in Test Example 3 to obtain the change in absorbance of the sample for total bilirubin therein. In addition, a control sample having a known bilirubin concentration was tested in the same manner to obtain the change in absorbance of the control sample. From the data thus obtained, the total bilirubin concentration in the serum sample was obtained according to the above-mentioned equation (1). Briefly, the control sample used herein was a 1:1 mixture of a direct bilirubin reagent and an indirect bilirubin reagent having a known bilirubin concentration. The results obtained are shown in Table 9 below.

TABLE 9

| Precursor of Reaction Promoter | Total Bilirubin (mg/dl) |
| --- | --- |
| 2,6-Dibromo-4-(N-γ-glutamyl)aminophenol | 4.84 |

EXAMPLE 6

The following reagent kits were prepared, which are for measuring direct bilirubin.
Promoter reagent 1:
0.1M lactic acid-trisodium citrate buffer (pH 3.7) containing 0.3% Triton X-100 and 69.87 μM 4-amino2,6-dichlorophenol-β-D-galactopyranoside.
Enzyme Reagent 1:
10 mM potassium phosphate buffer (pH 6.0) containing 0.3% Triton X-100, 400 U/ml of ascorbate oxidase and 10 U/ml of β-galactosidase.

EXAMPLE 7

The following reagent kits were prepared, which are for measuring total bilirubin.
Promoter Reagent 2:
20 mM POPSO (pH 8.0) buffer containing 0.5% sodium sulfate, 0.25% SDS, 0.2% sodium cholate, 20 mM glycylglycine and 75.75 μM 2,6-dibromo-4-(N-γ-glutamyl)aminophenol.
Enzyme Reagent 2:
20 mM POPSO (pH 8.0) buffer containing 20 mM glycylglycine, 160 U/ml of ascorbate oxidase and 1 U/ml of γ-glutamyl transferase.

EXAMPLE 8:

The reagents as prepared in Example 6 and Example 7 were stored in a cool and dark place at 10° C. for predetermined duration of storage as in Table 10 below, and then tested as hereinunder. 0.1 ml of a normal human serum sample was added to 2.2 ml of the Promoter Reagent 1 and preincubated for 5 minutes, and 0.75 ml of the Enzyme Reagent 1 was added thereto and reacted for 5 minutes. Then, the change in absorbance of the reaction solution was measured to obtain the direct bilirubin concentration in the sample. In the same manner, 0.1 ml of the same, normal human serum sample was added to 2.2 ml of the Promoter Reagent 2 and preincubated for 5 minutes, and 0.75 ml of the Enzyme Reagent 2 was added thereto and reacted for 5 minutes. Then the change in absorbance of the reaction solution was measured to obtain the total bilirubin concentration in the sample. Apart from the serum sample, a control sample having a known bilirubin concentration was processed in the same manner as above, and the change in absorbance of the control sample was obtained. From the data thus obtained, the direct bilirubin concentration and the total bilirubin concentration in the serum sample were obtained according to the above-mentioned equation (1). The results obtained are shown in Table 10. The normal human serum sample used herein had a direct bilirubin content of 0.24 mg/dl, as measured with a direct bilirubin measuring kit (Direct Bilirubin II-HA Test Wako, produced by Wako Jun-yaku Kogyo KK), and had a total bilirubin content of 0.74 mg/dl, as measured with a total bilirubin measuring kit (Total Bilirubin II-HA Test Wako, produced by Wako Jun-yaku Kogyo KK). The reagents used herein were stable and could be used in measuring bilirubin even after having been stored in aqueous solutions for 28 days.

TABLE 10

| Duration of Storage of Kits after Their Preparation (day) | Direct Bilirubin (mg/dl) | Total Bilirubin (mg/dl) |
| --- | --- | --- |
| 0 | 0.26 | 0.77 |
| 7 | 0.25 | 0.76 |
| 14 | 0.25 | 0.77 |
| 21 | 0.28 | 0.79 |
| 28 | 0.27 | 0.76 |

As has been described in detail hereinabove, the present invention uses an enzyme, ascorbate oxidase, which is more stable than bilirubin oxidase, along with a reaction promoter for the enzyme, and it is possible to rapidly and accurately measure the amount of bilirubin in a sample according to the present invention.

In addition, the present invention may also use a precursor of reaction promoter along with an enzyme capable of decomposing it into an active reaction promoter. The precursor of reaction promoter can keep stable in solution for a long period of time. Therefore, even after having been stored long, the reagent of the present invention comprising such a precursor of reaction promoter can be used to accurately measure the content of bilirubin in a sample.

Conventional enzyme-containing reagents to be used in measuring bilirubin must be provided in the form of freeze-dried products, which must be formulated into bilirubin-measuring preparations just before use. Different from such troublesome, conventional reagents, the bilirubin-measuring reagents of the present invention can be provided in the form of stable solutions which can be directly used in measuring bilirubin.

While the invention has been described in detail and with reference to specific embodiments thereof, it will be apparent to one skilled in the art that various changes and modifications can be made therein without departing from the spirit and scope thereof.

What is claimed is:

1. A method for quantitative determination of bilirubin in a sample, comprising the steps of (A),(B),(C) and (D):

(A) selecting a reaction promoter selected from the group consisting of a), b) and c):
   a) substituted aromatic hydrocarbon with at least two substituents which are independently selected from substituted amino, unsubstituted amino and hydroxyl,
   b) substituted aromatic heterocyclic compound with at least two substituents which are independently selected from substituted amino, unsubstituted amino and hydroxyl, and
   c) organic iron compound, (B) subjecting the bilirubin in the sample to coexist with ascorbate oxidase and the reaction promoter in an aqueous medium to thereby oxidize the bilirubin, (C) measuring a change in absorbance of the aqueous medium, and (D) comparing the change in absorbance with a calibration curve.

2. The method according to claim 1, wherein the aromatic hydrocarbon is selected from the group consisting of benzene, naphthalene and anthracene.

3. The method according to claim 1, wherein the aromatic heterocyclic compound is selected from the group consisting of pyridine, pyrazine, pyridazine, quinoline, isoquinoline, quinoxaline, quinazoline, cinnoline, phthalazine and naphthyridine.

4. The method according to claim 1, wherein the substituted amino is a substituted or unsubstituted alkyl-substituted amino.

5. The method according to claim 1, wherein the substituted aromatic hydrocarbon and the substituted aromatic heterocyclic compound with at least two substituents are substituted by additional 1 to 4 substituents which are independently selected from halogen and substituted or unsubstituted alkyl.

6. The method according to claim 1, wherein the organic iron compound is selected from hexacyanoferrate, substituted or unsubstituted ferrocene and iron chelate.

7. The method according to claim 1, wherein the reaction promoter is selected from the compound of the general formula (I):

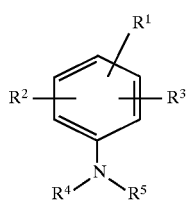

wherein $R^1$ represents hydroxyl, or substituted or unsubstituted amino; $R^2$ and $R^3$ may be the same or different, and each represents hydrogen, halogen, or substituted or unsubstituted alkyl; $R^4$ and $R^5$ may be the same or different, and each represents hydrogen, or substituted or unsubstituted alkyl;

and the compound of the general formula (II):

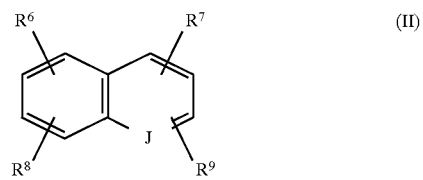

wherein $R^6$, $R^7$, $R^8$ and $R^9$ may be the same or different, and at least two of the $R^6$, $R^7$, $R^8$ and $R^9$ are independently selected from substituted amino, unsubstituted amino and hydroxyl, and the remains are independently selected from hydrogen, halogen, hydroxyl, substituted amino, unsubstituted amino, substituted alkyl and unsubstituted alkyl; J represents CH or N.

8. The method according to claim 1, wherein the aqueous medium is a buffer.

9. The method according to claim 1, wherein the bilirubin is a direct bilirubin and the aqueous medium is a buffer of pH 2.0 to 4.5.

10. The method according to claim 1, wherein the bilirubin is a total bilirubin and the aqueous medium is a buffer of pH 5.0 to 12.0.

11. A method for quantitative determination of bilirubin in a sample, comprising the steps of (A),(B),(C) and (D):

(A) selecting a precursor of reaction promoter selected from the group consisting of a) and b):
   a) substituted aromatic hydrocarbon with at least two substituents which are independently selected from substituted amino, unsubstituted amino and hydroxyl, and at least one of which substituents is protected with an enzymatically-removable protective group, and
   b) substituted aromatic heterocyclic compound with at least two substituents which are independently selected from substituted amino, unsubstituted amino and hydroxyl, and at least one of which substituents is protected with an enzymatically-removable protective group, (B) subjecting the bilirubin in the sample to coexist with ascorbate oxidase, the precursor of reaction promoter and an enzyme having the activity of removing the protective group from the substituent in the substituted aromatic hydrocarbon or substituted aromatic heterocyclic compound in an aqueous medium to thereby oxidize the bilirubin, (C) measuring a change in absorbance of the aqueous medium, and (D) comparing the change in absorbance with a calibration curve.

12. The method according to claim 11, wherein the aromatic hydrocarbon is selected from the group consisting of benzene, naphthalene and anthracene.

13. The method according to claim 11, wherein the aromatic heterocyclic compound is selected from the group consisting of pyridine, pyrazine, pyridazine, quinoline, isoquinoline, quinoxaline, quinazoline, cinnoline, phthalazine and naphthyridine.

14. The method according to claim 11, wherein the substituted amino is a substituted or unsubstituted alkyl-substituted amino.

15. The method according to claim 11, wherein the substituted aromatic hydrocarbon and the substituted aromatic heterocyclic compound with at least two substituents are substituted by additional 1 to 4 substituents which are independently selected from halogen and substituted or unsubstituted alkyl.

16. The method according to claim 11, wherein the precursor of reaction promoter is selected from the compound of the general formula (III):

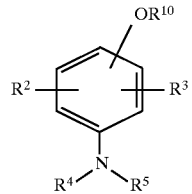

wherein $R^2$ and $R^3$ may be the same or different, and each represents hydrogen, halogen, or substituted or unsubstituted alkyl; $R^4$ and $R^5$ maybe the same or different, and each represents hydrogen, or substituted or unsubstituted alkyl; $R^{10}$ represents a saccharide residue;

and the compound of the general formula (IV):

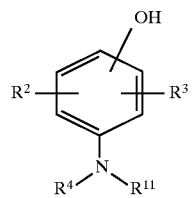

wherein $R^2$ and $R^3$ may be the same or different, and each represents hydrogen, halogen, or substituted or unsubstituted alkyl; $R^4$ represents hydrogen, or substituted or unsubstituted alkyl; $R^{11}$ represents an amino acid residue.

17. The method according to claim 11, wherein the enzymatically-removable protective group is an amino acid residue for the substituted or unsubstituted amino substituent, or a saccharide residue, phospho or sulfo for the hydroxyl substituent.

18. The method according to claim 11, wherein the aqueous medium is a buffer.

19. The method according to claim 11, wherein the bilirubin is a direct bilirubin and the aqueous medium is a buffer of pH 2.0 to 4.5.

20. The method according to claim 11, wherein the bilirubin is a total bilirubin and the aqueous medium is a buffer of pH 5.0 to 12.0.

21. A reagent for quantitative determination of bilirubin, comprising ascorbate oxidase and a reaction promoter selected from the group consisting of a), b) and c):
   a) substituted aromatic hydrocarbon with at least two substituents which are independently selected from substituted amino, unsubstituted amino and hydroxyl,
   b) substituted aromatic heterocyclic compound with at least two substituents which are independently selected from substituted amino, unsubstituted amino and hydroxyl, and
   c) organic iron compound.

22. A kit for quantitative determination of bilirubin, comprising (A) and (B):
   (A) a reagent comprising ascorbate oxidase, and
   (B) a reagent comprising a reaction promoter selected from the group consisting of a), b) and c):
      a) substituted aromatic hydrocarbon with at least two substituents which are independently selected from substituted amino, unsubstituted amino and hydroxyl,
      b) substituted aromatic heterocyclic compound with at least two substituents which are independently selected from substituted amino, unsubstituted amino and hydroxyl, and
      c) organic iron compound.

23. A reagent for quantitative determination of bilirubin, comprising ascorbate oxidase, a precursor of reaction promoter selected from the group consisting of a) and b):
   a) substituted aromatic hydrocarbon with at least two substituents which are independently selected from substituted amino, unsubstituted amino and hydroxyl, and at least one of which substituents is protected with an enzymatically-removable protective group, and
   b) substituted aromatic heterocyclic compound with at least two substituents which are independently selected from substituted amino, unsubstituted amino and hydroxyl, and at least one of which substituents is protected with an enzymatically-removable protective group; and an enzyme having the activity of removing the protective group from the substituent in the substituted aromatic hydrocarbon or substituted aromatic heterocyclic compound.

24. A kit for quantitative determination of bilirubin, comprising (A), (B) and (C):
   (A) a reagent comprising ascorbate oxidase,
   (B) a reagent comprising a precursor of reaction promoter selected from the group consisting of a) and b):
      a) substituted aromatic hydrocarbon with at least two substituents which are independently selected from substituted amino, unsubstituted amino and hydroxyl, and at least one of which substituents is protected with an enzymatically-removable protective group, and
      b) substituted aromatic heterocyclic compound with at least two substituents which are independently selected from substituted amino, unsubstituted amino and hydroxyl, and at least one of which substituents is protected with an enzymatically-removable protective group, and
   (C) a reagent comprising an enzyme having the activity of removing the protective group from the substituent in the substituted aromatic hydrocarbon or substituted aromatic heterocyclic compound.

25. A kit for quantitative determination of bilirubin, comprising (A) and (B):
   (A) a reagent comprising a precursor of reaction promoter selected from the group consisting of a) and b):
      a) substituted aromatic hydrocarbon with at least two substituents which are independently selected from substituted amino, unsubstituted amino and hydroxyl, and at least one of which substituents is protected with an enzymatically-removable protective group, and
      b) substituted aromatic heterocyclic compound with at least two substituents which are independently selected from substituted amino, unsubstituted amino and hydroxyl, and at least one of which substituents is protected with an enzymatically-removable protective group, and
   (B) a reagent comprising ascorbate oxidase and an enzyme having the activity of removing the protective group from the substituent in the substituted aromatic hydrocarbon or substituted aromatic heterocyclic compound.

26. A kit for quantitative determination of bilirubin, comprising (A) and (B):
   (A) a reagent comprising ascorbate oxidase and a precursor of reaction promoter selected from the group consisting of a) and b):
      a) substituted aromatic hydrocarbon with at least two substituents which are independently selected from substituted amino, unsubstituted amino and hydroxyl, and at least one of which substituents is protected with an enzymatically-removable protective group, and b) substituted aromatic heterocyclic compound with at least two substituents which are independently selected from substituted amino, unsubstituted amino and hydroxyl, and at least one of which substituents is protected with an enzymatically-removable protective group, and (B) a reagent comprising an enzyme having the activity of removing the protective group from the substituent in the substituted aromatic hydrocarbon or substituted aromatic heterocyclic compound.

* * * * *

UNITED STATES PATENT AND TRADEMARK OFFICE
CERTIFICATE OF CORRECTION

PATENT NO.   :  5,858,695

DATED        :  January 12, 1999

INVENTOR(S)  :  AKIRA KADOTA, ET AL.

It is certified that error appears in the above-identified patent and that said Letters Patent is hereby corrected as shown below:

Title page,
AT [56] REFERENCES CITED

FOREIGN PATENT DOCUMENTS

```
"027656
 159487
 017999" should read
--56-027656
  57-159487
  59-017999--; and
"4267893" should read --4-267893--.
```

COLUMN 1

```
Line 5, "f or" should read --for--;
Line 21, "known is a method" should read
         --a method is known--; and
Line 29, "known are methods using" should read
         --methods are known which use--.
```

UNITED STATES PATENT AND TRADEMARK OFFICE
CERTIFICATE OF CORRECTION

PATENT NO.  : 5,858,695

DATED       : January 12, 1999

INVENTOR(S) : AKIRA KADOTA, ET AL.

It is certified that error appears in the above-identified patent and that said Letters Patent is hereby corrected as shown below:

COLUMN 4

Line 15, "practical" should read --be practically--;
    Line 37, Close up right margin;
    Line 38, close up left margin; and
    Line 46, "zineandnaphthyridine;
         andmorepreferredarequinoline," should read
         --zinc and naphthyridine; and more preferred are
         quinoline,--.

COLUMN 5

Line 30, "be also be as" should read --also be--; and
    Line 31, "may" should read --and may--.

COLUMN 6

Line 12, "remains" should read --rest--; and
    Line 52, "preferable" should read --preferably--.

UNITED STATES PATENT AND TRADEMARK OFFICE
CERTIFICATE OF CORRECTION

PATENT NO. : 5,858,695

DATED : January 12, 1999

INVENTOR(S) : AKIRA KADOTA, ET AL.

It is certified that error appears in the above-identified patent and that said Letters Patent is hereby corrected as shown below:

COLUMN 7

Line 3, "form" should read --from--;
    Line 5, "have" should read --has--;
    Line 25, "may" should read --may be--; and
    Line 35, "those" should read --as those--.

COLUMN 8

Line 17, "can be" should be deleted;
    Line 18, "used" should be deleted; and
    Line 25, "γglutamyl" should read --γ-glutamyl--.

COLUMN 9

Line 14, "cloudness" should read --cloudiness--;
    Line 15, "to" should read --in--;
    Line 16, "the" should be deleted;
    Line 34, "cloudness of the sample to" should read
        --cloudiness of the sample in--;
    Line 54, "change" should read --changes--; and
    Line 55, "construct" should read --construct a--.

UNITED STATES PATENT AND TRADEMARK OFFICE
CERTIFICATE OF CORRECTION

PATENT NO. : 5,858,695

DATED : January 12, 1999

INVENTOR(S) : AKIRA KADOTA, ET AL.

It is certified that error appears in the above-identified patent and that said Letters Patent is hereby corrected as shown below:

COLUMN 10

Line 18, "There agent" should read --The reagent--; and
    Line 57, "comprising" should read --comprises--.

COLUMN 11

Line 3, "and" should read --¶ and--;
    Line 39, "potassiumphosphate" should read
        --potassium phosphate--;
    Line 45, "as" should be deleted;
    Line 46, "as" should read --by-- and
        "simplewording" should read --simple wording--;
        and
    Line 53, "almost" should read --effectively--.

COLUMN 12

Line 30, "Asergillus" should read --Aspergillus--.

UNITED STATES PATENT AND TRADEMARK OFFICE
CERTIFICATE OF CORRECTION

PATENT NO. : 5,858,695

DATED : January 12, 1999

INVENTOR(S) : AKIRA KADOTA, ET AL.

It is certified that error appears in the above-identified patent and that said Letters Patent is hereby corrected as shown below:

COLUMN 14

Line 5, "almost" should read --significantly--; and
    Line 43, "was" should read --there was--.

COLUMN 15

Line 40, "0.1" should read --¶0.1--.

COLUMN 17

Line 45, "4-amino2,6-" should read --4-amino-2,6- --.

COLUMN 18

Line 2, "0.1" should read --¶0.1--.

COLUMN 20

Line 12, "remains" should read --rest--.

UNITED STATES PATENT AND TRADEMARK OFFICE
CERTIFICATE OF CORRECTION

PATENT NO.  : 5,858,695

DATED       : January 12, 1999

INVENTOR(S) : AKIRA KADOTA, ET AL.

It is certified that error appears in the above-identified patent and that said Letters Patent is hereby corrected as shown below:

COLUMN 21

Line 14, "maybe" should read --may be--.

Signed and Sealed this

Ninth Day of November, 1999

Attest:

Attesting Officer

Q. TODD DICKINSON

Acting Commissioner of Patents and Trademarks